(12) United States Patent
Doepfer et al.

(10) Patent No.: US 10,253,376 B2
(45) Date of Patent: Apr. 9, 2019

(54) DNA-BASED DETECTION AND IDENTIFICATION OF EIGHT MASTITIS PATHOGENS

(71) Applicant: Wisconsin Alumni Research Foundation, Madison, WI (US)

(72) Inventors: Doerte Doepfer, Middleton, WI (US); Kelly Anklam, Dane, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 490 days.

(21) Appl. No.: 14/512,937

(22) Filed: Oct. 13, 2014

(65) Prior Publication Data

US 2015/0104799 A1 Apr. 16, 2015

Related U.S. Application Data

(60) Provisional application No. 61/891,628, filed on Oct. 16, 2013.

(51) Int. Cl.
*C12Q 1/689* (2018.01)
*C12Q 1/6844* (2018.01)

(52) U.S. Cl.
CPC ........... *C12Q 1/689* (2013.01); *C12Q 1/6844* (2013.01); *C12Q 2600/16* (2013.01)

(58) Field of Classification Search
None
See application file for complete search history.

(56) References Cited

U.S. PATENT DOCUMENTS

2009/0191561 A1* 7/2009 Holopainen ......... C12Q 1/6883
435/6.16

FOREIGN PATENT DOCUMENTS

| JP | 2006271370 A | 10/2006 |
|---|---|---|
| JP | 2007189980 A | 8/2007 |
| JP | 2008125376 A | 6/2008 |
| JP | 2010284090 A | 12/2010 |
| JP | 2012060925 A | 3/2012 |
| WO | 2009006743 A1 | 1/2009 |

OTHER PUBLICATIONS

Pinnow et al. Journal of Dairy Science 2001; 84: 1640-1645.*
Lee et al. Journal of Veterinary Diagnostic Investigation 2008; 20: 463-471.*
Nagamine et al. Molecular and Cellular Probes 2002; 16: 223-229.*
Tie et al. Journal of Biomedicine and Biotechnology 2012; 2012: 435982 (5 pages).*
Hong et al. World Journal of Microbiology and Biotechnology 2012; 28: 523-531.*
Shao et al. International Journal of Food Microbiology 2011; 148: 75-79.*
Neuberger et al. Journal of Clinical Microbiology 2008; 46: 377-379.*
Tanner et al. BioTechniques 2012; 53: 81-89.*
Fang et al. Analytical Chemistry 2010; 82: 3002-3006 (Year: 2010).*
European Patent Office, Communication—Partial European Search Report, dated Mar. 15, 2015 in the matter of EP14189060.8.
D. Wang, et al; Rapid and Sensitive Detection of *Escherichia coli* 0157 in Raw Milk by Loop-mediated Isothermal Amplification Combined with Chemosensor; Milchwissenschaft 2012; Food Sci & Eng Coll., Xuchang Unvi., Xuchang 461000; vol. 67, No. 4, p. 385 Sep. 1, 2012 China.
D. Wang, et al.; Development and Evaluation of a Loop-Mediated Isothermal Amplification Method for Detecting *Escherichia coli* 0157 in Raw Milk; Journal of Rapid Methods and Automation in Microbiology, vol. 17, No. 1, pp. 55-56, Mar. 2, 2009 XP055165032, ISSN: 1060-3999, DOI: 10.1111/j.1745-4581.2008.00151.
J. Nemoto, et al.; Rapid Detection of Shiga toxin-producing *Escherichia coli* by Multiplex LAMP, a new DNA Amplification Method, Abstracts of the General Meeting of the American Society for Microbiology, vol. 103, p. 501, Jan. 1, 2003 XP009109834, ISSN: 1060-2011 United States.
D. Wang, et al.; Development and evaluation of a loop-mediated isothermal amplification (LAMP) method for detecting *Staphylococcus aureus* in raw milk. Milchwissenschaft, VV GMBH Volkswirtschaftlicher Verlag, vol. 64, No. 4, Jan. 1, 2009 (Jan. 1, 2009), pp. 368-371, XP009182110! ISSN: 0026-3788 Munchen, DE.
X. Zhao, et al. Loop-mediated Isothermal 1-15 Amplification Assay Targeting the femA Gene for Rapid Detection of *Staphylococcus aureus* from Clinical and Food Samples, Journal of Microbiology and Biotechnology 2013 Korean Society for Microbiology and Biotechnology Kor, vol. 23, No. 2, Feb. 2013, (Feb. 2013), pp. 246-250, XP002735011, ISSN: 1017-7825.
N. Sowmya, et al.; Rapid and simple DNA 1-15 extraction Method for the Detection of Enterotoxigenic *Staphylococcus aureus* Directly from Food Samples: Comparison of PCR and LAMP Methods, Journal of Applied Microbiology, vol. 113, No. 1, Jul. 15, 2012 (Jul. 15, 2012), pp. 106-113, XP055164533, ISSN: 1364-5072! DOI: 10.1111jj.1365-2672.2012.05315.
Tie Zhang , et al.; Loop-Mediated Isothermal Amplification for Detection of *Staphylococcus aureus* in Dairy Cow Suffering from Mastitis, Journal of Biomedicine and Biotechnology, vol. 66, No. 10, Jan. 1, 2012 (Jan. 1, 2012), pp. 1851-1855, XP055164534, ISSN: 1110-7243, DOI: 10.1006/bbrc.2001.5921.
Clinton Torres, et al.; LAVA: An Open-Source Approach to Designing LAMP (Loop-Mediated Isothermal Amplification) DNA Signatures; BMC Bioinformatics, vol. 12, No. 1, Jan. 1, 2011 (Jan. 1, 2011), p. 240, XP055164863, ISSN: 1471-2105, DOI: 10.1373/clinchem.2004.032011.
Y. Kimura, et al.; Optimization of 1-15 turn-back primers in isothermal amplification; Nucleic Acids Research, vol. 39, No. 9, May 1, 2011 (May 1, 2011), pp. e59-e59, XP055164865, ISSN: 0305-1048, DOI: 10.1093/narjgkr041.

(Continued)

*Primary Examiner* — Angela M. Bertagna
(74) *Attorney, Agent, or Firm* — Quarles & Brady LLP

(57) ABSTRACT

LAMP primer sets for detecting eight mastitis pathogens are disclosed. Methods and kits of using the primer sets to simultaneously detect at least two of the eight mastitis pathogens are also described.

14 Claims, 1 Drawing Sheet
(1 of 1 Drawing Sheet(s) Filed in Color)

Specification includes a Sequence Listing.

(56) References Cited

OTHER PUBLICATIONS

Wang, et al; Rapid Detection Viable *Escherichia coli* 0157 in Raw Milk Using Loop-Mediated Isothermal Amplification with Aid of Ethidium Monoazide; Advanced Materials Research, vol. 343-344; Sep. 1, 2011 (Sep. 1, 2011), pp. 1217-1221, XP055164221, DOI: 10.4018/www.scientific.net/AMR.343-344.1217.

Bai, et al., Development of a Loop-Mediated Isothermal Amplification Assay for Sensitive and Rapid Detection of Mycoplasma Bovis, African Journal of Biotechnology, 2011, 10(57):12333-12338.

Fan, et al., Application of Loop-Mediated Isothermal Amplification (LAMP) in Rapid Detection of *Mycobacterium tuberculosis*, Modern Food Science and Technology, 2008, 24(8):835-838.

European Patent Office, Extended Search Report and Opinion, Application No. 14189060.8, dated Jul. 30, 2015, 27 pages.

* cited by examiner

SEQUENCE LISTING

<160> NUMBER OF SEQ ID NOS: 47

<210> SEQ ID NO 1
<211> LENGTH: 18
<212> TYPE: DNA
<213> ORGANISM: Escherichia coli

<400> SEQUENCE: 1
cgaactgaac tggcagac                       18

<210> SEQ ID NO 2
<211> LENGTH: 20
<212> TYPE: DNA
<213> ORGANISM: Escherichia coli

<400> SEQUENCE: 2
ttcaacgctg acatcaccat                     20

<210> SEQ ID NO 3
<211> LENGTH: 45

```
<212> TYPE: DNA
<213> ORGANISM: Escherichia coli

<400> SEQUENCE: 3
ggcatagtta aagaaatcat ggaagggaat ggtgattacc gacga            45

<210> SEQ ID NO 4
<211> LENGTH: 35
<212> TYPE: DNA
<213> ORGANISM: Escherichia coli

<400> SEQUENCE: 4
tacaccacgc cgaacaccgt ggttacagtc ttgcg                       35

<210> SEQ ID NO 5
<211> LENGTH: 21
<212> TYPE: DNA
<213> ORGANISM: Escherichia coli

<400> SEQUENCE: 5
gactgctttt tcttgccgtt t                                      21

<210> SEQ ID NO 6
<211> LENGTH: 16
<212> TYPE: DNA
<213> ORGANISM: Escherichia coli

<400> SEQUENCE: 6
cgtggtgacg catgtc                                            16

<210> SEQ ID NO 7
<211> LENGTH: 25
<212> TYPE: DNA
<213> ORGANISM: Staphylococcus aureus

<400> SEQUENCE: 7
aacaagcgag ataacttaca acaac                                  25

<210> SEQ ID NO 8
<211> LENGTH: 22
<212> TYPE: DNA
<213> ORGANISM: Staphylococcus aureus

<400> SEQUENCE: 8
ggtcaatgcc atgatttaat gc                                     22

<210> SEQ ID NO 9
<211> LENGTH: 47
<212> TYPE: DNA
<213> ORGANISM: Staphylococcus aureus

<400> SEQUENCE: 9
agaaaccagc agagataggt aagatgcaaa tgagcaaaag attgaag          47

<210> SEQ ID NO 10
<211> LENGTH: 43
<212> TYPE: DNA
<213> ORGANISM: Staphylococcus aureus

<400> SEQUENCE: 10
gaagttgttt attatgctgg tggtaatcat ttcccattgc act              43

<210> SEQ ID NO 11
```

```
<211> LENGTH: 19
<212> TYPE: DNA
<213> ORGANISM: Klebsiella pneumoniae

<400> SEQUENCE: 11
ggaagtgtgg ataaacggc                                                 19

<210> SEQ ID NO 12
<211> LENGTH: 19
<212> TYPE: DNA
<213> ORGANISM: Klebsiella pneumoniae

<400> SEQUENCE: 12
ggatggtcaa cccaacgat                                                 19

<210> SEQ ID NO 13
<211> LENGTH: 36
<212> TYPE: DNA
<213> ORGANISM: Klebsiella pneumoniae

<400> SEQUENCE: 13
cctgctcggt gttattgagg acagcgtggg ttttcc                              36

<210> SEQ ID NO 14
<211> LENGTH: 39
<212> TYPE: DNA
<213> ORGANISM: Klebsiella pneumoniae

<400> SEQUENCE: 14
ttcgtctgct ggtggtgctg gattgagcgg ataatagat                           39

<210> SEQ ID NO 15
<211> LENGTH: 18
<212> TYPE: DNA
<213> ORGANISM: Klebsiella pneumoniae

<400> SEQUENCE: 15
aaagtgtggc agataccg                                                  18

<210> SEQ ID NO 16
<211> LENGTH: 20
<212> TYPE: DNA
<213> ORGANISM: Klebsiella pneumoniae

<400> SEQUENCE: 16
ccaacaagaa atacaaccgc                                                20

<210> SEQ ID NO 17
<211> LENGTH: 23
<212> TYPE: DNA
<213> ORGANISM: Streptococcus uberis

<400> SEQUENCE: 17
ggtattgaaa aagcaacatc agc                                            23

<210> SEQ ID NO 18
<211> LENGTH: 22
<212> TYPE: DNA
<213> ORGANISM: Streptococcus uberis

<400> SEQUENCE: 18
ggtcaaattg catcccttca ac                                             22
```

```
<210> SEQ ID NO 19
<211> LENGTH: 44
<212> TYPE: DNA
<213> ORGANISM: Streptococcus uberis

<400> SEQUENCE: 19
caactttttc tgaacgtgat gacactattg cccaaccagt ttcc            44

<210> SEQ ID NO 20
<211> LENGTH: 41
<212> TYPE: DNA
<213> ORGANISM: Streptococcus uberis

<400> SEQUENCE: 20
ggagtatatc tcagaagccc aagttctgtt tccataccac g               41

<210> SEQ ID NO 21
<211> LENGTH: 19
<212> TYPE: DNA
<213> ORGANISM: Streptococcus uberis

<400> SEQUENCE: 21
acttgggcaa tagcctctt                                        19

<210> SEQ ID NO 22
<211> LENGTH: 21
<212> TYPE: DNA
<213> ORGANISM: Streptococcus uberis

<400> SEQUENCE: 22
gtgtaggcaa tgatggtgtt a                                     21

<210> SEQ ID NO 23
<211> LENGTH: 20
<212> TYPE: DNA
<213> ORGANISM: Streptococcus dysgalactiae

<400> SEQUENCE: 23
gcgacttatg ttgccaatgc                                       20

<210> SEQ ID NO 24
<211> LENGTH: 20
<212> TYPE: DNA
<213> ORGANISM: Streptococcus dysgalactiae

<400> SEQUENCE: 24
agcgtcaaat gaaccgaagg                                       20

<210> SEQ ID NO 25
<211> LENGTH: 44
<212> TYPE: DNA
<213> ORGANISM: Streptococcus dysgalactiae

<400> SEQUENCE: 25
gcttgacgaa tatcttctgg aatacctga aataggtgaa aacc             44

<210> SEQ ID NO 26
<211> LENGTH: 41
<212> TYPE: DNA
<213> ORGANISM: Streptococcus dysgalactiae

<400> SEQUENCE: 26
cggaggacat ttaaaccatt ccttgagcaa catcaggagt g               41
```

```
<210> SEQ ID NO 27
<211> LENGTH: 22
<212> TYPE: DNA
<213> ORGANISM: Streptococcus dysgalactiae

<400> SEQUENCE: 27
ggttacatct gccaataatt cc                                              22

<210> SEQ ID NO 28
<211> LENGTH: 20
<212> TYPE: DNA
<213> ORGANISM: Streptococcus dysgalactiae

<400> SEQUENCE: 28
gtccccagaa aaacaagacg                                                 20

<210> SEQ ID NO 29
<211> LENGTH: 23
<212> TYPE: DNA
<213> ORGANISM: Streptococcus agalactiae

<400> SEQUENCE: 29
agttcagctt ttacgactct tag                                             23

<210> SEQ ID NO 30
<211> LENGTH: 23
<212> TYPE: DNA
<213> ORGANISM: Streptococcus agalactiae

<400> SEQUENCE: 30
caacataaag tgattactca gcc                                             23

<210> SEQ ID NO 31
<211> LENGTH: 47
<212> TYPE: DNA
<213> ORGANISM: Streptococcus agalactiae

<400> SEQUENCE: 31
gcaatagaac ccttcattaa gacaagcatt acaacaggtt atgacat                   47

<210> SEQ ID NO 32
<211> LENGTH: 39
<212> TYPE: DNA
<213> ORGANISM: Streptococcus agalactiae

<400> SEQUENCE: 32
caacgaagcc actgtctctt tctccatcag cattacgca                            39

<210> SEQ ID NO 33
<211> LENGTH: 20
<212> TYPE: DNA
<213> ORGANISM: Mycoplasma bovis

<400> SEQUENCE: 33
gcttatctcg gctatacctg                                                 20

<210> SEQ ID NO 34
<211> LENGTH: 26
<212> TYPE: DNA
<213> ORGANISM: Mycoplasma bovis

<400> SEQUENCE: 34
ctatgttcta attcttttgg tctttg                                          26
```

<210> SEQ ID NO 35
<211> LENGTH: 39
<212> TYPE: DNA
<213> ORGANISM: Mycoplasma bovis

<400> SEQUENCE: 35
aggcaaagtc atttctaggt gtcaaggaac cccaccaga 39

<210> SEQ ID NO 36
<211> LENGTH: 43
<212> TYPE: DNA
<213> ORGANISM: Mycoplasma bovis

<400> SEQUENCE: 36
tgactatgaa aaagaaccac cattatggtg catcagggtg aag 43

<210> SEQ ID NO 37
<211> LENGTH: 20
<212> TYPE: DNA
<213> ORGANISM: Mycoplasma bovis

<400> SEQUENCE: 37
tcaccgatag gtaagtttgc 20

<210> SEQ ID NO 38
<211> LENGTH: 24
<212> TYPE: DNA
<213> ORGANISM: Mycoplasma bovis

<400> SEQUENCE: 38
aatagtcatc ataaagcagc aacg 24

<210> SEQ ID NO 39
<211> LENGTH: 18
<212> TYPE: DNA
<213> ORGANISM: Staphylococcus epidermidis

<400> SEQUENCE: 39
ccgtgttgaa cgtggtca 18

<210> SEQ ID NO 40
<211> LENGTH: 19
<212> TYPE: DNA
<213> ORGANISM: Staphylococcus epidermidis

<400> SEQUENCE: 40
ggwgtratwg arccaggag 19

<210> SEQ ID NO 41
<211> LENGTH: 45
<212> TYPE: DNA
<213> ORGANISM: Staphylococcus epidermidis

<400> SEQUENCE: 41
ttacggaaca tttctacacc wgtgtgaaga agttgaaatc atcgg 45

<210> SEQ ID NO 42
<211> LENGTH: 40
<212> TYPE: DNA
<213> ORGANISM: Staphylococcus epidermidis

<400> SEQUENCE: 42

```
tggtgacaac atyggtgctt gctaatactt gwccacgttg                                40

<210> SEQ ID NO 43
<211> LENGTH: 21
<212> TYPE: DNA
<213> ORGANISM: Artificial Sequence
<220> FEATURE:
<223> OTHER INFORMATION: BETA-lactamase blaR1

<400> SEQUENCE: 43
caggtatagt aaacgggaag t                                                   21

<210> SEQ ID NO 44
<211> LENGTH: 22
<212> TYPE: DNA
<213> ORGANISM: Artificial Sequence
<220> FEATURE:
<223> OTHER INFORMATION: BETA-lactamase blaR1

<400> SEQUENCE: 44
ataacatccc attcagccat ag                                                  22

<210> SEQ ID NO 45
<211> LENGTH: 45
<212> TYPE: DNA
<213> ORGANISM: Artificial Sequence
<220> FEATURE:
<223> OTHER INFORMATION: BETA-lactamase blaR1

<400> SEQUENCE: 45
ctttccatct gataaatgtg tagcaatggg tggtttgtag gttac                         45

<210> SEQ ID NO 46
<211> LENGTH: 43
<212> TYPE: DNA
<213> ORGANISM: Artificial Sequence
<220> FEATURE:
<223> OTHER INFORMATION: BETA-lactamase blaR1

<400> SEQUENCE: 46
ccatctggga aaaatgctga aggccattta aaacacccat ttc                           43

<210> SEQ ID NO 47
<211> LENGTH: 262
<212> TYPE: DNA
<213> ORGANISM: Mycoplasma bovis

<400> SEQUENCE: 47
atacatgagc gcttatctcg gctatacctg aaaatgatga tgagagatta ttctcaattc         60
aaggaacccc accagatatg gcaaaccttg cctatcggtg accctttgc acctagaaat         120 gactttgcct tagaaattga ctatgaaaaa gaaccaccat taattgaaat taatagtcat         180
cataaagcag caacgtgact accttcaccc tgatgcacca aaaatacaaa gaccaaaaga         240
attagaacat agactaaaaa gt                                                 262
```

DNA-BASED DETECTION AND IDENTIFICATION OF EIGHT MASTITIS PATHOGENS

CROSS-REFERENCE TO RELATED APPLICATIONS

This application claims the benefit of U.S. Provisional Patent Application Ser. No. 61/891,628 filed Oct. 16, 2013.

STATEMENT REGARDING FEDERALLY SPONSORED RESEARCH OR DEVELOPMENT

N/A.

BACKGROUND OF THE INVENTION

Bovine mastitis is a persistent inflammation of the udder usually caused by bacterial infections. It is generally spread through contact with contaminated milking equipment or other materials. Presently, the only treatment for the disease is through long-acting antibiotics. Milk from cows undergoing mastitis treatment cannot be marketed until the drugs have cleared their systems.

Mastitis has been estimated to cost the US Dairy industry $1.7 B-$2 B/yr. There are two levels of diagnosed disease: (1) clinical mastitis characterized by visual signs of the disease and poor milk quality and (2) subclinical mastitis which is characterized by a high somatic cell count in the milk. The milk from cows showing subclinical mastitis is cultured to detect whether pathogenic bacteria are present. This testing requires that the lab plate the milk and wait a 1-2 days to see whether bacterial strains grow on the plates. Those strains can then be identified by their metabolic reactions or by using PCR-based assays to determine the type of bacteria present. Clinical mastitis causes the greatest financial loss through lowered milk production, so ways of catching the disease early are needed to mitigate the overall loss, and to prevent spread of the disease.

Therefore, there is a need to develop fast and economical mastitis assays.

SUMMARY OF THE INVENTION

In one embodiment, the present invention is a nucleotide primer set for LAMP amplification, used for detecting *E. coli* comprising (a) a F3 primer having a sequence identical or substantially identical to SEQ ID NO:1, (b) a B3 primer having a sequence identical or substantially identical to SEQ ID NO:2, (c) a FIP primer having a sequence identical or substantially identical to SEQ ID NO:3, (d) a BIP primer having a sequence identical or substantially identical to SEQ ID NO:4, (e) a LF primer having a sequence identical or substantially identical to SEQ ID NO:5, and (f) a LB primer having a sequence identical or substantially identical to SEQ ID NO:6.

In one embodiment, the present invention is a nucleotide primer set for LAMP amplification, used for detecting *Staphylococcus aureus* comprising (a) a F3 primer having a sequence identical or substantially identical to SEQ ID NO:7, (b) a B3 primer having a sequence identical or substantially identical to SEQ ID NO:8, (c) a FIP primer having a sequence identical or substantially identical to SEQ ID NO:9, and (d) a BIP primer having a sequence identical or substantially identical to SEQ ID NO:10.

In one embodiment, the present invention is a nucleotide primer set for LAMP amplification, used for detecting *Klebsiella pneumonia* comprising (a) a F3 primer having a sequence identical or substantially identical to SEQ ID NO:11, (b) a B3 primer having a sequence identical or substantially identical to SEQ ID NO:12, (c) a FIP primer having a sequence identical or substantially identical to SEQ ID NO:13, (d) a BIP primer having a sequence identical or substantially identical to SEQ ID NO:14, (e) a LF primer having a sequence identical or substantially identical to SEQ ID NO:15, and (f) a LB primer having a sequence identical or substantially identical to SEQ ID NO:16.

In one embodiment, the present invention is a nucleotide primer set for LAMP amplification, used for detecting *Streptococcus uberis* comprising (a) a F3 primer having a sequence identical or substantially identical to SEQ ID NO:17, (b) a B3 primer having a sequence identical or substantially identical to SEQ ID NO:18, (c) a FIP primer having a sequence identical or substantially identical to SEQ ID NO:19, (d) a BIP primer having a sequence identical or substantially identical to SEQ ID NO:20, (e) a LF primer having a sequence identical or substantially identical to SEQ ID NO:21, and (f) a LB primer having a sequence identical or substantially identical to SEQ ID NO:22.

In one embodiment, the present invention is a nucleotide primer set for LAMP amplification, used for detecting *Streptococcus dysgalactiae* comprising (a) a F3 primer having a sequence identical or substantially identical to SEQ ID NO:23, (b) a B3 primer having a sequence identical or substantially identical to SEQ ID NO:24, (c) a FIP primer having a sequence identical or substantially identical to SEQ ID NO:25, (d) a BIP primer having a sequence identical or substantially identical to SEQ ID NO:26, (e) a LF primer having a sequence identical or substantially identical to SEQ ID NO:27, and (f) a LB primer having a sequence identical or substantially identical to SEQ ID NO:28.

In one embodiment, the present invention is a nucleotide primer set for LAMP amplification, used for detecting *Streptococcus agalactiae* comprising (a) a F3 primer having a sequence identical or substantially identical to SEQ ID NO:29, (b) a B3 primer having a sequence identical or substantially identical to SEQ ID NO:30, (c) a FIP primer having a sequence identical or substantially identical to SEQ ID NO:31, and (d) a BIP primer having a sequence identical or substantially identical to SEQ ID NO:32.

In one embodiment, the present invention is a nucleotide primer set for LAMP amplification, used for detecting *Mycoplasma bovis* comprising (a) a F3 primer having a sequence identical or substantially identical to SEQ ID NO:33, (b) a B3 primer having a sequence identical or substantially identical to SEQ ID NO:34, (c) a FIP primer having a sequence identical or substantially identical to SEQ ID NO:35, (d) a BIP primer having a sequence identical or substantially identical to SEQ ID NO:36, (e) a LF primer having a sequence identical or substantially identical to SEQ ID NO:37, and (f) a LB primer having a sequence identical or substantially identical to SEQ ID NO:38.

In one embodiment, the present invention is a nucleotide primer set for LAMP amplification, used for detecting coagulase-negative *Staphylococci* (CNS) tuf or any one of the subtypes including *S. epidermidis, S. chromogenes*, and *S. simulans*, comprising (a) a F3 primer having a sequence identical or substantially identical to SEQ ID NO:39, (b) a B3 primer having a sequence identical or substantially identical to SEQ ID NO:40, (c) a FIP primer having a sequence identical or substantially identical to SEQ ID NO:41, and (d) a BIP primer having a sequence identical or substantially identical to SEQ ID NO:42.

In one embodiment, the present invention is a LAMP primer panel for simultaneously detecting two or more mastitis pathogens in a sample comprising (a) two or more primer sets designed to detect at least two pathogens selected from the group consisting of *E. coli, Staphylococcus aureus, Klebsiella pneumonia, Streptococcus uberis, Streptococcus dysgalactiae, Streptococcus agalactiae, Mycoplasma bovis*, and coagulase-negative *Staphylococci* (CNS) tuf including subtypes *S. epidermidis, S. chromogenes*, and *S. simulans*, wherein each or every primer set is capable of amplifying a specific region of the respective mastitis pathogen.

In one embodiment, the present invention is a reaction solution suitable for the primer system of claim 1, comprising:
(a) betaine in the concentration range of 0.5-1.5 M;
(b) dNTP in the concentration range of 1-1.6 mM;
(c) $Mg^{2+}$ in the concentration range of 5.5-7 mM; and
(d) Bst DNA polymerase in the concentration range of 8-10 units.

In one embodiment, the present invention is a LAMP method of simultaneously detecting two or more mastitis pathogens in a sample comprising the steps of (a) extracting DNA from the sample; (b) amplifying a specific region of the mastitis pathogen by reacting the extracted DNA of step (a) with the primer panel described above; and (c) detecting or identifying the presence or absence of the amplified products of at least two mastitis pathogens.

In one embodiment, the present invention is a kit for simultaneously detecting or identifying at least two mastitis pathogens in a sample comprising (a) at least two primer sets designed to detect at least two pathogens selected from the group consisting of *E. coli, Staphylococcus aureus, Klebsiella pneumonia, Streptococcus uberis, Streptococcus dysgalactiae, Streptococcus agalactiae, Mycoplasma bovis*, and coagulase-negative *Staphylococci* (CNS) tuf including subtypes *S. epidermidis, S. chromogenes*, and *S. simulans*. Preferably, the kit comprises the reaction solution described above.

BRIEF DESCRIPTION OF THE DRAWINGS

The patent or application file contains at least one drawing in color. Copies of this patent or patent application publication with color drawings will be provided by the Office upon request and payment of the necessary fee.

DETAILED DESCRIPTION OF THE INVENTION

Figure 1:
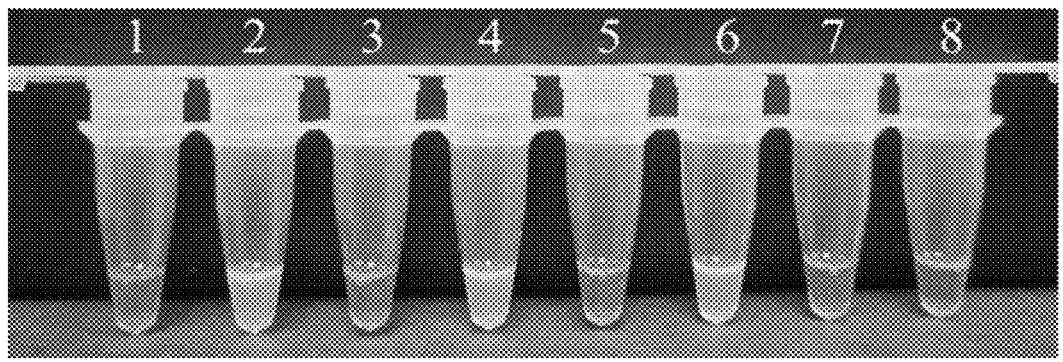
FIG. 1 is a visualization of LAMP amplification products with SYBR Green I (observed by naked eye). Green indicates a positive result and orange indicates a negative result.

The present invention relates to assays for simultaneously detecting and identifying the presence of eight relevant mastitis pathogens, or any subset of the eight pathogens, by using loop-mediated isothermal DNA amplification (LAMP). In one embodiment of the invention, β-lactamase blaR1 (GenBank M62650.1) is also detected.

Compared to current bacteriological culture methods used for bovine mastitis diagnostics, the assays of the present invention save at least one to two days before informed antimicrobial therapy can be started while applying extremely low-cost instruments (a mini centrifuge and a mini heat block). Compared to conventional and real-time PCR, the assays of the present invention save at least four hours running times and time for gel electrophoresis during conventional PCR and do not require the analysis of amplification curves to determine Ct values for real-time PCR.

The assays can work on DNA extractions from milk or from bacteriological cultures (colonies on agar plates or broth cultures). Extensive validation and exclusion of cross reactions have contributed to the ongoing validation of the assays in practice and laboratory settings. The assays of the present invention can be taught to the audiences in need of such assays, including developing countries, within a day.

Specifically, the assays involve a DNA extraction (preferably about 35 min) combined with a LAMP running time of, preferably, about 47 min for the eight separate assays simultaneously. The inventors also developed a "one-for-all" master mix that can be used as a LAMP reaction solution for all eight pathogen specific primer sets at low volumes, preferably 20-50 micro liters, so the LAMP for amplifying the DNA of all eight pathogen can run under the same conditions.

The assays can be implemented under field and laboratory conditions as a diagnostic kit. In addition, milking robots or large-scale sample strings in routine diagnostic laboratories could use these assays for in-line testing. Such kits can be made available to farmers, laboratories and veterinary practices that perform base level mastitis diagnostics.

In sum, the assays of the present invention have at least one of four advantages: (1) combination of up to eight pathogens run under the same conditions, (2) time-saving and cost-saving conditions, (3) low cost instruments suitable for field/lab diagnostics, and (4) potential for the automization of the assays.

Exemplary embodiments of the present invention are described below.

Primers and Primer Sets

In its first aspect, the present invention provides LAMP primer sets for detecting up to eight relevant mastitis pathogens including *E. coli, Staphylococcus aureus, Klebsiella pneumonia, Streptococcus uberis, Streptococcus dysgalactiae, Streptococcus agalactiae, Mycoplasma bovis*, and coagulase-negative *Staphylococci* (CNS) tuf. The primer set of CNS tuf can also be used to detect any one of three subtypes of CNS including *S. epidermidis, S. chromogenes* and *S. simulans*, or all three subtypes at once.

"Loop-mediated Isothermal Amplification" (LAMP) is a type of "strand displacement" amplification, which utilizes a specially designed set of oligonucleotide primers, and a specific thermophilic DNA polymerase derived from *Bacillus stearothermophilus* (Y. Mori, et al., *BMC Biotechnol*, 2006, 6:3). The primers are designed to promote the formation of 'hairpin-loop' structures during the initial stages of the reaction, allowing high levels of self-primed DNA synthesis to occur from these structures as the reaction continues. In brief, the LAMP reaction is initiated by annealing and extension of a pair of "loop-forming" primers, followed by annealing and extension of a pair of flanking primers. Extension of these primers results in strand-displacement of the loop-forming elements, which fold up to form terminal hairpin-loop structures. Once these key structures have appeared, the amplification process becomes self-sustaining, and proceeds in a continuous and exponential manner (rather than a cyclic manner, like PCR) until all of the nucleotides (e.g., dATP, dTTP, dCTP & dGTP) in the reaction mixture have been incorporated into the amplified DNA. Normally, the target sequence which is amplified is typically 200-300 base-pairs (bp) in length, and the reaction relies upon recognition of between 120 bp and 160 bp of this sequence by several primers simultaneously during the amplification process.

Eight primer sets have been developed to detect specific mastitis pathogens including *E. coli, Staphylococcus aureus, Klebsiella pneumonia, Streptococcus uberis, Streptococcus dysgalactiae, Streptococcus agalactiae, Mycoplasma bovis,* and coagulase-negative *Staphylococci* (CNS) tuf including subtypes *S. epidermidis, S. chromogenes,* and *S. simulans.*

Specifically, each primer set comprises four oligonucleotide primers recognizing six distinct regions (F1, F2, F3, B1, B2 and B3) on the target DNA, including (1) the forward inner primer (FIP) consist of F1 complementary sequence and F2 direct sequence, (2) the back inner primer (BIP) consist of B1 direct sequence and B2 complementary sequence, (3) the first outer primer (F3 primer) and (4) the second outer primer (B3 primer). All these primers are designed to work at a constant temperature between 60° C. and 65° C. and the amplification results can typically be read within 45 minutes.

To accelerate implication reactions, the primer set may comprise one or two additional loop primers such as LF primer and LB primer. In the presence of either one of or both of LF and LB primers, the reaction can be accelerated due to the increasing number of reactions sites.

Examples of the primer sets of the present invention include (1) A LAMP primer set for detecting *E. coli* (GenBank HM221282.1) comprising the following primers:

```
F3 primer:
                                         (SEQ ID NO: 1)
CGAACTGAACTGGCAGAC B3 primer:
                                         (SEQ ID NO: 2)
TTCAACGCTGACATCACCAT FIP primer:
                                         (SEQ ID NO: 3)
GGCATAGTTAAAGAAATCATGGAAGGGAATGGTGATTACCGACGA BIP primer:
                                         (SEQ ID NO: 4)
TACACCACGCCGAACAC-CGTGGTTACAGTCTTGCG
and optionally LF primer:
                                         (SEQ ID NO: 5)
GACTGCTTTTTCTTGCCGTTT LB primer:
                                         (SEQ ID NO: 6)
CGTGGTGACGCATGTC.
```

(2) A LAMP primer set for detecting *Staphylococcus aureus* (GenBank GQ284641.1) comprising the following primers:

```
F3 primer:
                                         (SEQ ID NO: 7)
AACAAGCGAGATAACTTACAACAAC B3 primer:
                                         (SEQ ID NO: 8)
GGTCAATGCCATGATTTAATGC FIP primer:
                                         (SEQ ID NO: 9)
AGAAACCAGCAGAGATAGGTAAGATGCAAATGAGCAAAAGATTGAAG BIP primer:
                                         (SEQ ID NO: 10)
GAAGTTGTTTATTATGCTGGTGG-TAATCATTTCCCATTGCACT GC.
```

(3) A LAMP primer set for detecting *Klebsiella pneumonia* (GenBank AF293352.1) comprising the following primers:

```
F3 primer:
                                         (SEQ ID NO: 11)
GGAAGTGTGGATAAACGGC B3 primer:
                                         (SEQ ID NO: 12)
GGATGGTCAACCCAACGAT FIP primer:
                                         (SEQ ID NO: 13)
CCTGCTCGGTGTTATTGAG-GACAGCGTGGGTTTTCC BIP primer:
                                         (SEQ ID NO: 14)
TTCGTCTGCTGGTGGTG-CTGGATTGAGCGGATAATAGAT
and optionally LF primer:
                                         (SEQ ID NO: 15)
AAAGTGTGGCAGATACCG LB primer:
                                         (SEQ ID NO: 16)
CCAACAAGAAATACAACCGC.
```

(4) A LAMP primer set for detecting *Streptococcus uberis* (GenBank AF485804.1) comprising the following primers:

```
F3 primer:
                                         (SEQ ID NO: 17)
GGTATTGAAAAAGCAACATCAGC B3 primer:
                                         (SEQ ID NO: 18)
GGTCAAATTGCATCCCTTCAAC FIP primer:
                                         (SEQ ID NO: 19)
CAACTTTTTCTGAACGTGATGACA-CTATTGCCCAACCAGTTTCC BIP primer:
                                         (SEQ ID NO: 20)
GGAGTATATCTCAGAAGCC-CAAGTTCTGTTTCCATACCACG
and optionally LF primer:
                                         (SEQ ID NO: 21)
ACTTGGGCAATAGCCTCTT LB primer:
                                         (SEQ ID NO: 22)
GTGTAGGCAATGATGGTGTTA
```

(5) A LAMP primer set for detecting *Streptococcus dysgalactiae* (GenBank JF789446.1) comprising the following primers:

```
F3 primer:
                                         (SEQ ID NO: 23)
GCGACTTATGTTGCCAATGC B3 primer:
                                         (SEQ ID NO: 24)
AGCGTCAAATGAACCGAAGG
```

FIP primer:
(SEQ ID NO: 25)
GCTTGACGAATATCTTCTGGAAT-ACCCTGAAATAGGTGAAAACC

BIP primer:
(SEQ ID NO: 26)
CGGAGGACATTTAAACCATTC-CTTGAGCAACATCAGGAGTG
and optionally LF primer:
(SEQ ID NO: 27)
GGTTACATCTGCCAATAATTCC LB primer:
(SEQ ID NO: 28)
GTCCCCAGAAAAACAAGACG (6) A LAMP primer set for detecting *Streptococcus agalactiae* (GenBank AF093787.2) comprising the following primers:

F3 primer:
(SEQ ID NO: 29)
AGTTCAGCTTTTACGACTCTTAG

B3 primer:
(SEQ ID NO: 30)
CAACATAAAGTGATTACTCAGCC

FIP primer:
(SEQ ID NO: 31)
GCAATAGAACCCTTCATTAAGAC-AAGCATTACAACAGGTTATGACAT

BIP primer:
(SEQ ID NO: 32)
CAACGAAGCCACTGTCTCT-TTCTCCATCAGCATTACGCA.

(7) A LAMP primer set for detecting *Mycoplasma bovis* (GenBank AF130119.1) comprising the following primers:

F3 primer:
(SEQ ID NO: 33)
    GCTTATCTCGGCTATACCTG

B3 primer:
(SEQ ID NO: 34)
    CTATGTTCTAATTCTTTTGGTCTTTG

FIP primer:
(SEQ ID NO: 35)
    AGGCAAAGTCATTTCTAGGTG-TCAAGGAACCCCACCAGA

BIP primer:
(SEQ ID NO: 36)
    TGACTATGAAAAAGAACCACCATTA-TGGTGCATCAGGGTGAAG
    and optionally LF primer:
(SEQ ID NO: 37)
    TCACCGATAGGTAAGTTTGC LB primer:
(SEQ ID NO: 38)
    AATAGTCATCATAAAGCAGCAACG.

(8) A LAMP primer set for detecting coagulase-negative *Staphylococci* (CNS) tuf (GenBank AF298800.1, EU652790.1, HM352952.1, EU652822.1, AF298805.1) and *S. epidermidis, S. chromogenes,* and *S. simulans* comprising the following primers:

F3 primer:
(SEQ ID NO: 39)
CCGTGTTGAACGTGGTCA

B3 primer:
(SEQ ID NO: 40)
GGWGTRATWGARCCAGGAG

FIP primer:
(SEQ ID NO: 41)
TTACGGAACATTTCTACACCWGT-GTGAAGAAGTTGAAATCAT CGG

BIP primer:
(SEQ ID NO: 42)
TGGTGACAACATYGGTGCTT-GCTAATACTTGWCCACGTTG

In one embodiment of the invention, β-lactamase blaR1 (GenBank M62650.1) is also detected via the following primers:

F3 primer
(SEQ ID NO: 43)
CAGGTATAGTAAACGGGAAGT

B3 primer
(SEQ ID NO: 44)
ATAACATCCCATTCAGCCATAG

FIP primer
(SEQ ID NO: 45)
CTTTCCATCTGATAAATGTGTAGC-AATGGGTGGTTTGTAGGTTAC

BIP primer
(SEQ ID NO: 46)
CCATCTGGGAAAAATGCTGAA-GGCCATTTAAAACACCCATTTC

Of course, one skilled in the art would understand that the primers of the present invention include the primers that have the sequences substantially identical to SEQ ID NOs: 1-42 as described above. A primer is "substantially identical" if the primer comprises a sequence having modifications as compared to the sequence of SEQ ID NOs: 1-42 but the functions and activities of amplifying the target DNA are maintained. The modifications include, but are not limited to, substitution, deletion, insertion, and/or addition of one or more nucleic bases. There is also no limitation on the number or sites of nucleic bases that can be modified in the sequences of SEQ ID NOs: 1-42. Preferably, an average of 4 bp per 20 bp bases, or more preferably, an average of 2 bp per 20 bp bases are modified, removed or added.

In some embodiments, primers with substantial identical sequence to SEQ ID NOs: 1-42 are the oligonucleotides that have or maintain at least 80%, at least 85%, or preferably at least 90%, or more preferably 95% of the functions of the primers having the sequences of SEQ ID NOs: 1-42.

A primer with a sequence substantial identical to any one of SEQ ID NOs: 1-42 also includes the oligonucleotide with the aforementioned functions and activities and comprising a sequence similar to the sequence of any one of SEQ ID NOs: 1-42. The level of similarity or identity is not limited as long as the oligonucleotide has an aforementioned functions and activities; however, normally, the primers have at least 80%, at least 85%, preferably at least 90%, more preferably at least 95%, and most preferably at least 98% sequence identity with the sequences of SEQ ID NOs: 1-42.

As used herein, "% sequence identity" is determined by properly aligning respective oligonucleotide segments, or their complementary strands, with appropriate considerations for nucleotide insertions and deletions. When the sequences which are compared do not have the same length, "% sequence identity" refers to the percentage of the number of identical nucleotide residues between the sequences being compared in the total number of nucleotide residues in the longer sequence.

In some specific embodiments, the primers of SEQ ID NOs: 1-42 can be modified by up to 20% or average 4 bp per 20 bp, or preferably up to 10% or average 2 bp per 20 bp of oligonucleotide sequence, and at the same time meet at least one of, or preferably all, of the following criteria:
(1) The $T_m$ (melting temperature) for each primer domain is 57-62° C.;
(2) Limited self-hybridization potential of the primer— e.g. the primers were checked for their potential to generate false positive results by self-hybridization and were found to not do that;
(3) Both ends of the FIP and BIP primers should not be AT-rich and they have less than 50% AT base pairs;
(4) The length between primers sites '5 of F2 to '5 of F1 and '5 of B2 to '5 of B1 should be 40-60 bp; and/or
(5) The length of the amplified DNA region (F2 to B2) should not be longer than 200 bp.

Also, each primer in a primer set as described above can be used separately or in combinations with other suitable primers. For example, one may use one or more primers in a primer set and replace or substitute other primers in the set with suitable or equivalent primers.

Once the nucleic acid sequence of a primer is determined, the primer can be made by any means known in the art. For example, the primer can be chemically synthesized or ordered from commercial vendors.

Moreover, the primers of the present invention may be labeled for detection. Suitable labels, and methods for labeling primers are known in the art. For example, the labels include, without limitation, radioactive labels, biotin labels, fluorescent labels, chemiluminescent labels, bioluminescent labels, metal chelator labels and enzyme labels.

Primer Panels

Primer sets can be used separately in an assay to detect the respective pathogen, or preferably, two or more primer sets are used in a panel to detect two or more mastitis pathogens.

Thus, in its second aspect, the present invention provides a LAMP primer panel for simultaneously detecting two or more mastitis pathogens of *E. coli, Staphylococcus aureus, Klebsiella pneumonia, Streptococcus uberis, Streptococcus dysgalactiae, Streptococcus agalactiae, Mycoplasma bovis*, and coagulase-negative *Staphylococci* (CNS). The panel comprises two or more primer sets as described above, wherein each or every primer set is capable of amplifying a specific region of the respective mastitis pathogen.

When making a primer panel, any two or more of the described primer sets can be arranged into any combination. The combination can be made randomly or purposely to meet the need of detecting the mastitis pathogens of interest in a sample. For example, a primer panel may contain the primer sets for *E. coli* and *Staphylococcus aureus* to detect the presence of either or both pathogens. If needed, the panel may contain an additional primer set for *Streptococcus uberis*, either to detect or to eliminate the possibility of a suspicious affections or contamination caused by *Streptococcus uberis*.

Master Mix

In its third aspect, the present invention provides a reaction solution, termed "master mix" that is compatible with eight LAMP primer sets as described above. With this master mix, the assays can be used to detect all eight pathogens or any subset of the eight pathogens under the same conditions at the same time.

Specifically, the master mix comprises Betaine, dNTP, $Mg^{2+}$ and *Bacillus stearothermophilus* (Bst) DNA Polymerase. It may also additionally comprise nuclease free $H_2O$ or 1× polymerase buffer, or both.

The concentration of each components of the master mix can be determined to meet specific primers. For example, the master mix comprises:
(1) Betaine in the range of about 0.5 M - 1.5 M, and preferably 1.0 M;
(2) dNTP in the range of about 1 mM-1.6 mM, and preferably 1.2 mM;
(3) $Mg^{2+}$ in the range of about 5.5 mM-7 mM, and preferably 6 mM; and
(4) *Bacillus stearothermophilus* (Bst) DNA Polymerase in the range of about 8-10 units, and preferably 8 units.

In a preferred embodiment, the master mix comprises:
(1) about 1 M Betaine;
(2) about 1.2 mM dNTP;
(3) about 6 mM $Mg^{2+}$, such as 6 mM $MgSO_4$;
(4) about 8 units Bst DNA Polymerase;
(5) Nuclease Free $H_2O$; and
(6) 1× Polymerase buffer.

All these ingredients can be obtained through means known in the art. For example, they all are commercially available.

Of course, the ingredients of the Master Mix can be presented in different forms or substituted by equivalents. For example, $Mg^{2+}$ can be presented in magnesium sulfate or magnesium chloride. Betaine is used to reduce the formation of secondary structures in G-C rich region and improve amplification by enhancing the specificity of the PCR. This could be achieved by using other PCR additives such as ethylene glycol or 1,2-propanediol instead of Betaine.

Methods of Detecting Mastitis Pathogens

In its fourth aspect, the present invention provides methods of simultaneously detecting two or more mastitis pathogens in a sample comprising the steps of (a) extracting DNA from the sample; (b) amplifying a specific region of the mastitis pathogen by reacting the extracted DNA of step (a) with the primer panel as described above, which comprises at least two primer sets for the respective mastitis pathogens; and (c) detecting or identifying the presence or absence of the amplified products of at least two mastitis pathogens.

The term "simultaneous detection" as used herein means that the detection of at least two mastitis pathogens within a sample can be carried out in a same assay at the same or at different times. The term "at different times" as used herein means that one of the detection is carried out before or after the second detection in the same assay. The simultaneous detection also means that the detection of one mastitis pathogen is carried out shortly after the detection of another pathogen. For instance, when detecting two mastitis pathogens, the two pathogens can be detected in a LAMP assay at the same time, or the first pathogen is detected before or after the second pathogens is detected in the same LAMP assay.

The "simultaneous detection" also implies that the detections for different pathogens are carried out in the same platform or by the same device. For instance, a simultaneous detection can be carried out by using various sample containers, each comprising a different primer set for the respective pathogen and LAMP reactions in each containers is performed at the same time on the same device. Alternatively, the DNA sample to be tested may be comprised within in the same sample container so that a single sample is subjected to multiple detection steps or assays comprising the different primer sets for the respective pathogens. The simultaneous detection as described in the present application thus offers a convenient assaying method for measuring a plurality of mastitis pathogens in the same sample within a short period of time through LAMP reactions using the described primer sets or panel.

The term "sample" as used herein refers to any kind of sample to be tested for the presence of the pathogens. For example, a sample may be obtained from a biological subject, including sample of biological tissue or fluid origin obtained in vivo or in vitro. Such samples can be, but are not limited to, body fluid (e.g., milk, blood, blood plasma, serum, or urine), organs, tissues, fractions, cells isolated from mammals. Samples may include sections of the biological sample including tissues (e.g., sectional portions of an organ or tissue). Samples may also include extracts from a biological sample, for example, an antigen or a nucleic acid from a biological fluid (e.g., milk, blood, urine or the environment). Samples also include a sample not derived from a biological subject, for example, a solution that contains bacteria.

In some embodiments, the sample is derived from a mammalian (e.g., rat, mouse, cow, dog, donkey, guinea pig, or rabbit). In some embodiments, the sample is derived from humans.

In some preferred embodiments, the sample is derived from mammalian milk. Examples of milk include, but are not limited to, cow's milk (bovine milk), camel milk, buffalo milk, goat's milk, sheep's milk, and sow milk. Optionally the milk is acidified, e.g. by addition of an acid (such as citric, acetic or lactic acid), or mixed, e.g. with water. The milk may be raw or processed, e.g. by filtering, sterilizing, pasteurizing, homogenizing etc, or it may be reconstituted dried milk. A preferred example of "bovine milk" according to the present invention is pasteurized cow's milk. It is understood that the milk may be acidified, mixed or processed before, during and/or after the inoculation with bacteria.

In other preferred embodiments, the samples also include bacterial culture derived from mammalian milk, such as, the bacterial colonies grown on a culturing plate.

The term "DNA extraction" or "DNA isolation" used herein refers to a process of purification of DNA from sample using a combination of physical and chemical methods. The DNA extraction can be performed by any methods known in the art. For example, a typical DNA extraction procedure involves cell disruption or cell lysis to expose the DNA, removing membrane lipids by adding a detergent or surfactants which may also serve in cell lysis, removing proteins by adding a protease (optional), and removing RNA by adding an RNase (optional).

In some embodiments, the DNA can be purified and extracted using commercially available DNA extraction kits, such as MagMAX™ Total Nucleic Acid Isolation Kit and QIAamp® DNA Mini-prep Kit.

The term "amplification" used herein refers to a template-dependent process that results in an increase in the concentration of a nucleic acid molecule relative to its initial concentration. As used herein, the term "template-dependent process" refers to a process that involves the template-dependent extension of a primer molecule where the sequence of the newly synthesized strand of nucleic acid is dictated by the well-known rules of complementary base pairing. For example, a sequence of one nucleic acid molecule is said to be the "complement" of another if it contains a T (or U), A, C, or G at a position in which the other molecule contains an A, T (or U), G or C, respectively.

The amplification can be performed by any methods known in the art. Exemplary amplification methods include PCR, LAMP, Strand Displacement Amplification (SDA), Ligase Chain Reaction (LCR), Transcription-Mediated-Amplification (TMA), Transcription-Reverse Transcription -Concerted method (TRC), Hybrid Capture (HC), microarray method, and so forth.

In a preferred embodiment, the DNA amplification of present invention is LAMP using the LAMP primer sets described above. For example, the LAMP amplification can be performed as follows: First, the reagents (for example, Bst DNA polymerase, a reaction buffer (Master Mix), the primer set, and distilled water) are mixed to prepare an amplification reaction solution. A detection reagent, for example, a fluorescent label, may also be mixed in this amplification reaction solution. Second, the DNA extraction is added to this amplification reaction solution, and the resultant mixture is incubated at 60-65° C., or preferably 65° C. for 30-60 minutes, or preferably 45 minutes. Third, the reaction is then inactivated at 80-95° C., or preferably 80° C. for 2-10 minutes, or preferably 2 minutes.

Detection or identification of a mastitis pathogen in a sample is conducted by examining the presence of the amplified respective DNA in the reaction solution. Any methods known in the art can be used for detection including, but not limited to, radiation, biotin, antibodies, fluorescence, chemiluminescence, bioluminescence, metal chelator labels and enzymes.

In a preferred embodiment, the detection or identification can be confirmed by fluorescence. In a fluorescence detection, a fluorescence detection reagent is added to carry out the reaction, and the color of the reaction solution is visually confirmed under a excitation light or confirmed by using fluorometer. More specifically, if the reaction solution emits fluorescence, a positive determination can be made, namely, that a mastitis pathogen DNA is amplified, while if the reaction solution does not emit fluorescence, a negative determination can be made, namely, that the mastitis pathogen DNA is not amplified. The difference between positive and negative for reaction solution fluorescence can be more clearly determined by using a UV irradiation apparatus.

In the flowing Examples, the inventors have demonstrated the assays for detecting all eight mastitis pathogens in DNA extractions from cow's milk or from bacteriological cultures (colonies on agar plates or broth cultures) derived from cow's milk. The assay involves a rapid DNA extraction method (35 to 50 min) combined with the 47 min running time for the eight separate assays simultaneously. Detection limits for the assay are the same as for PCR (1 CFU/ml after 3 hr enrichment of milk or $10^3$-$10^4$ CFU/ml in raw milk without enrichment).

Of course, the primer sets and the LAMP methods described above can be used to detect one mastitis pathogen at a time. Also, the methods of the present invention are not limited to cases in which the DNA is derived from bacterial culture from a milk sample. The method can also be applied where the DNA is directly extracted from milk. For example, *Mycoplasma bovis* is especially difficult to culture on agar plates, so having a detection method for detecting the presence of the bacteria in fluids could be useful for identifying the presence of this pathogen which causes respiratory disease, arthritis, and other diseases in cattle. The primer set and method can also be used to detect *Streptococcus* directly in milk. Also, the present invention can be used to detect *Staphylococci* from any samples obtained from a subject or a companion animal, including, but not limited to milk, skin, tissues, etc.

Thus, in its fifth aspect, the present invention provides methods of detecting or identifying *Mycoplasma bovis* in a sample comprising the steps of (a) extracting DNA from the sample or preferably directly from milk; (b) amplifying a specific region of the mastitis pathogen by reacting the extracted DNA of step (a) the primer set for *Mycoplasma bovis*; and (c) detecting or identifying the presence or absence of the amplified DNA products of *Mycoplasma bovis*.

In its sixth aspect, the present invention provides methods of detecting or identifying *Streptococcus uberis, Streptococcus dysgalactiae, Streptococcus dysgalactiae* or *Staphylococci* in a sample comprising the steps of (a) extracting DNA from the sample or preferably directly from milk; (b) amplifying a specific region of the mastitis pathogen by reacting the extracted DNA of step (a) the primer set for *Streptococcus uberis, Streptococcus dysgalactiae, Streptococcus dysgalactiae* or *Staphylococci*; and (c) detecting or identifying the presence or absence of the amplified products of *Streptococcus uberis, Streptococcus dysgalactiae, Streptococcus dysgalactiae* or *Staphylococci*.

One advantage of the methods described above for detecting *Mycoplasma bovis* or *Streptococcus* is that the assays can be carried out directly from milk without cell culturing on a plate.

Kits

The primer sets of the present invention can be provided in the form of a kit, singly or in combination. Thus, in its seventh aspect, the present invention is a kit for detecting mastitis pathogens, which comprises at least one primer set as described above. Preferably, the kit of the present invention comprises at least two primer sets so the kit can be used to simultaneously detect at least two mastitis pathogens.

Primer sets be housed or mixed together in a kit when used. However, in a preferred embodiment, each primer set is separated from the other primer sets in a kit. For example, primer sets can be added to or housed in a separate tube, a separate well of a plastic microtiter plate, or a separate chamber of a microfluidic chip.

The kit may additional comprise reagents (for example, Bst DNA polymerase, a reagent mixed solution for reaction such as Master Mix as disclosed herein) or other apparatus (for example, a reaction tube or a LAMP device), which are necessary for the implementation of the nucleic acid amplification reaction by the LAMP method. These reagents may need to be stored separate from the primers to maintain biological activities.

The assays of the present invention can also be automated. For example, the assay can be automated in the sense that the DNA extraction and multiple LAMP assay steps can be performed by an automatic pipetting and reaction device. The automated assays may also contain sampling parts that sort a milk sample upon a "flag event" such as increased somatic cell count, culture positive results or other events of interest to ensure heath and food safety. The automated sampling and assay could also be implemented in a milking robot or in the large-scale sampling routines in laboratories specialized in raw milk analysis or in dairy processing plants.

EXAMPLES

Example 1

Mastitis LAMP Assay Protocol

An exemplary protocol of a loop-mediated isothermal DNA amplification (LAMP) assay for mastitis and the sequences of the LAMP primer sets for eight mastitis pathogens is presented.

One would plate 100 μl of milk on TSA with 5% sheep blood and incubate overnight at 37° C. A single colony is selected and placed in 50 μl of nuclease-free $H_2O$ in a 1.5 ml microcentrifuge tube and vortex for 15 seconds. The mixture is then boiled for 20 minutes at 100° C. on a dry heat block. One would then vortex for 5 seconds and centrifuge for 20 minutes at 21,000×g. Then transfer 30 μl of the supernatant/DNA template to a new 1.5 ml tube for analysis by the LAMP assays stored at 4° C. Prepare Master Mix/Primer Mix for 1 more sample per 10 samples than actually running to ensure enough volume for all samples, keeping all components and samples on ice.

TABLE 1

| Master Mix - Primers | |
|---|---|
| Nuclease Free $H_2O$ | 4.5 μl |
| 3M Betaine | 8.3 μl |
| 10 mM dNTP | 3.0 μl |
| 10x Polymerase Buffer | 2.5 μl |
| 10 mM MgSO4 | 1.5 μl |
| Bst 1 Polymerase | 1.0 μl |
| | 20.8 μl |

TABLE 2

| Primer Mix | |
|---|---|
| 10 μM F3 Primer | 0.5 μl |
| 10 μM B3 Primer | 0.5 μl |
| 100 μM FIP Primer | 0.4 μl |
| 100 μM BIP Primer | 0.4 μl |
| 100 μM LF Primer or NF $H_2O$ | 0.2 μl |
| 100 μM LB Primer or NF $H_2O$ | 0.2 μl |
| | 2.2 μl |

Template 2.0 μl

Of the combination used, pipet 20.8 μl of Master mix—primers and 2.2 μl of Primer mix for each sample. Then pipet 23 μl of the above mix to 0.2 ml tubes and pipet 2.0 μl of nuclease free water for the NTC. Pipet 2.0 μl of each sample to appropriate tube and spin strip tubes for 5 seconds to remove any bubbles. Place tubes in dry heat block for 45 minutes at 65° C. followed by 2 minutes at 80° C. to stop the reaction. Remove tubes from heat block and add 1 μl of SYBR green 1 to each tube. Check for fluorescence with a hand held UV lamp. Confirmation may be performed by electrophoresis by analyzing 1 μl of the LAMP product on a 1.5% agarose gel at 80V for 1 hr. Stain gel for 20 min with Ethidium bromide and observe by using a gel imaging system.

| Primers | |
|---|---|
| *E. coli* uidA (GenBank HM221282.1) | |
| F3 | (SEQ ID NO: 1) |
| CGAACTGAACTGGCAGAC | |

-continued

| Primers | |
|---|---|
| B3<br>TTCAACGCTGACATCACCAT | (SEQ ID NO: 2) |
| FIP<br>GGCATAGTTAAAGAAATCATGGAAG-GGAATGGTGATTACCGACGA | (SEQ ID NO: 3) |
| BIP<br>TACACCACGCCGAACAC-CGTGGTTACAGTCTTGCG | (SEQ ID NO: 4) |
| LF<br>GACTGCTTTTTCTTGCCGTTT | (SEQ ID NO: 5) |
| LB<br>CGTGGTGACGCATGTC | (SEQ ID NO: 6) |

*Staphylococcus aureus* femA (GenBank GQ284641.1)

| | |
|---|---|
| F3<br>AACAAGCGAGATAACTTACAACAAC | (SEQ ID NO: 7) |
| B3<br>GGTCAATGCCATGATTTAATGC | (SEQ ID NO: 8) |
| FIP<br>AGAAACCAGCAGAGATAGGTAA-GATGCAAATGAGCAAAAGATTGAAG | (SEQ ID NO: 9) |
| BIP<br>GAAGTTGTTTATTATGCTGGTGG-TAATCATTTCCCATTGCACTGC | (SEQ ID NO: 10) |

*Klebsiella pneumonia* hemolysin gene (GenBank AF293352.1)

| | |
|---|---|
| F3<br>GGAAGTGTGGATAAACGGC | (SEQ ID NO: 11) |
| B3<br>GGATGGTCAACCCAACGAT | (SEQ ID NO: 12) |
| FIP<br>CCTGCTCGGTGTTATTGAG-GACAGCGTGGGTTTTCC | (SEQ ID NO: 13) |
| BIP<br>TTCGTCTGCTGGTGGTG-CTGGATTGAGCGGATAATAGAT | (SEQ ID NO: 14) |
| LF<br>AAAGTGTGGCAGATACCG | (SEQ ID NO: 15) |
| LB<br>CCAACAAGAAATACAACCGC | (SEQ ID NO: 16) |

*Streptococcus uberis* Cpn60 (GenBank AF485804.1)

| | |
|---|---|
| F3<br>GGTATTGAAAAAGCAACATCAGC | (SEQ ID NO: 17) |
| B3<br>GGTCAAATTGCATCCCTTCAAC | (SEQ ID NO: 18) |
| FIP<br>CAACTTTTTCTGAACGTGATGACA-CTATTGCCCAACCAGTTTCC | (SEQ ID NO: 19) |

-continued

| Primers | |
|---|---|
| BIP<br>GGAGTATATCTCAGAAGCC-CAAGTTCTGTTTCCATACCACG | (SEQ ID NO: 20) |
| LF<br>ACTTGGGCAATAGCCTCTT | (SEQ ID NO: 21) |
| LB<br>GTGTAGGCAATGATGGTGTTA | (SEQ ID NO: 22) |
| *Streptococcus dysgalactiae* sodA (GenBank JF789446.1)<br>F3<br>GCGACTTATGTTGCCAATGC | (SEQ ID NO: 23) |
| B3<br>AGCGTCAAATGAACCGAAGG | (SEQ ID NO: 24) |
| FIP<br>GCTTGACGAATATCTTCTGGAAT-ACCCTGAAATAGGTGAAAACC | (SEQ ID NO: 25) |
| BIP<br>CGGAGGACATTTAAACCATTC-CTTGAGCAACATCAGGAGTG | (SEQ ID NO: 26) |
| LF<br>GGTTACATCTGCCAATAATTCC | (SEQ ID NO: 27) |
| LB<br>GTCCCCAGAAAAACAAGACG | (SEQ ID NO: 28) |
| *Streptococcus agalactiae* cly (GenBank AF093787.2)<br>F3<br>AGTTCAGCTTTTACGACTCTTAG | (SEQ ID NO: 29) |
| B3<br>CAACATAAAGTGATTACTCAGCC | (SEQ ID NO: 30) |
| FIP<br>GCAATAGAACCCTTCATTAAGAC-AAGCATTACAACAGGTTATGACAT | (SEQ ID NO: 31) |
| BIP<br>CAACGAAGCCACTGTCTCT-TTCTCCATCAGCATTACGCA | (SEQ ID NO: 32) |
| *Mycoplasma bovis* opp (GenBank AF130119.1)<br>F3<br>GCTTATCTCGGCTATACCTG | (SEQ ID NO: 33) |
| B3<br>CTATGTTCTAATTCTTTTGGTCTTTG | (SEQ ID NO: 34) |
| FIP<br>AGGCAAAGTCATTTCTAGGTG-TCAAGGAACCCCACCAGA | (SEQ ID NO: 35) |
| BIP<br>TGACTATGAAAAGAACCACCATTA-TGGTGCATCAGGGTGAAG | (SEQ ID NO: 36) |
| LF<br>TCACCGATAGGTAAGTTTGC | (SEQ ID NO: 37) |

| Primers | |
|---|---|
| LB<br>AATAGTCATCATAAAGCAGCAACG | (SEQ ID NO: 38) |

CNS tuf (GenBank AF298800.1, EU652790.1, HM352952.1, EU652822.1, AF298805.1) and *Streptococcus epidermidis, Streptococcus chromogenes*, and *Streptococcus simulans*

```
F3
CCGTGTTGAACGTGGTCA                                    (SEQ ID NO: 39)

B3
GGWGTRATWGARCCAGGAG                                   (SEQ ID NO: 40)

FIP                                                   (SEQ ID NO: 41)
TTACGGAACATTTCTACACCWGT-GTGAAGAAGTTGAAATCATCGG

BIP                                                   (SEQ ID NO: 42)
TGGTGACAACATYGGTGCTT-GCTAATACTTGWCCACGTTG
```

Example 2

LAMP Diagram

Below is an example of LAMP amplification of the present invention:

```
LAMP Diagram
                                                      (SEQ ID NO: 47)
           F3 →                                              F2 →
181   atacat gagc gcttatctcg gctatacctg aaaatgatga tgagagatta ttctcaat tc ← LF
241   aaggaacccc accagata tg gcaaacttac ctatcgtga cccttttg ca cctagaaatg ← F1           B1 →                              LB →
301   actttgcct tagaaat tgac tatgaaaaag aaccaccatt aattgaaatt aatagtcatc ← B2
361   ataaagcagc aacgtgacta cttcaccctg atgcaccaaa aatacaaaga ccaaaagaat ← B3
421   tagaacatag actaaaaagt.

F3                                                    (SEQ ID NO: 33)
GCTTATCTCGGCTATACCTG

B3                                                    (SEQ ID NO: 34)
CTATGTTCTAATTCTTTTGGTCTTTG

FIP Reverse Complement F1
AGGCAAAGTCATTTCTAGGTG (F2)                                                  (SEQ ID NO: 35)
TCAAGGAACCCCACCAGA (SEQ ID NO: 36)
BIP B1
TGACTATGAAAAGAACCACCATTA (B2)
TGGTGCATCAGGGTGAAG
Reverse Complement LF                                                    (SEQ ID NO: 37)
TCACCGATAGGTAAGTTTGC
Reverse Complement LB                                                    (SEQ ID NO: 38)
AATAGTCATCATAAAGCAGCAACG
```

The LAMP assay relies on auto-cycling strand displacement DNA synthesis performed with the Bst DNA polymerase large fragment. The LAMP reaction requires a set of four oligonucleotide primers recognizing six distinct regions (F1, F2, F3, B 1, B2 and B3) on the target DNA: the forward inner primer (FIP) consist of F1 complementary sequence and F2 direct sequence, the back inner primer (BIP) consists of B1 direct sequence and B2 complementary sequence, and also the two outer primers (F3 primer and B3 primer). The reaction is performed at a constant temperature between 60 C and 65 C and results can be read within 45 min. With an additional one or two primers (LF primer and LB primer), termed 'loop primers', the reaction can be accelerated due to the increasing number of reaction sites. LAMP products can be detected indirectly by the turbidity that arises due to the formation of insoluble magnesium pyrophosphate. A large amount of pyrophosphate ions is produced as a by product, yielding a white precipitate of magnesium pyrophosphate in the reaction mixture. The increase in the turbidity of the reaction mixture caused by the production of precipitate correlates with the amount of DNA synthesized. Visual discrimination can be enhanced by adding 1 µl SYBR Green 1 to the reaction and visually detecting a color change by the naked eye or fluorescence under UV light.

Example 3

Mastitis LAMP Protocol

Below is an exemplary Mastitis LAMP protocol.

TABLE 3

| Optimized Reagent Conc. | Working Range |
| --- | --- |
| Nuclease Free H$_2$O | — |
| 1x Polymerase Buffer | — |
| 1M Betaine | 0.5M-1.5M |
| 1.2 mM dNTP | 1 mM-1.6 mM |
| 6 mM MgSO4 | 5.5 mM-7 mM |
| 8 units Bst DNA Polymerase | 8-10 units |
| 0.2 µM F3 Primer | 0.1 µM-0.3 µM |
| 0.2 µM B3 Primer | 0.1 µM-0.3 µM |
| 1.6 µM FIP Primer | 1.4 µM-1.8 µM |
| 1.6 µM BIP Primer | 1.4 µM-1.8 µM |
| 0.8 µM LF Primer | 0.8 µM-1.2 µM |
| 0.8 µM LB Primer | 0.8 µM-1.2 µM |
| Temperature 65° C. | 60-65° C. |
| Time at 65° C. 45 mins | 30-60 mins |
| Reaction inactivation temperature 80° C. | 80-95° C. |
| Reaction inactivation time 2 min | 2-10 min |

Primers are the same as those listed above.

The reaction is capable of working without the LF and/or LB primers. Betaine reduces the formation of secondary structures in G-C rich regions and improves amplification by enhancing the specificity of the PCR. This could possibly be achieved by using other PCR additives such as ethylene glycol or 1, 2-propanediol instead of betaine. Magnesium sulfate could be substituted with magnesium chloride.

Example 4

Mastitis LAMP Protocol

DNA Extraction Methods
Enrichment

One hundred microliters of milk was plated on TSA with 5% sheep blood and incubated overnight at 37° C. Bacterial colonies were added to 50 µl of nuclease-free water, and the suspension was boiled for 20 min at 100° C. After boiling the suspension was centrifuged at 21,00×g for 20 min. The supernatant was transferred to a clean microcentrifuge tube and used as DNA template for LAMP analyses.

Direct

One milliliter of milk was centrifuged at 21,00×g for 10 min and the pellet was resuspended in 100 µl of nuclease-free water. The suspension was boiled for 20 min at 100° C. After boiling the suspension was centrifuged at 21,00×g for 20 min. The supernatant was transferred to a clean microcentrifuge tube and used as DNA template for LAMP analyses. Two commercial extraction kits (MagMax total nucleic acid isolation kit-Ambion and QIAamp DNA mini kit-Qiagen) have been used according to manufacturer's instructions to isolate DNA directly from the milk. See attached protocols. All three of the above direct extraction methods could be applied to skin scrapings to detect dermatitis pathogens.

LAMP Reaction

Lamp assays were carried out in a total of 25 µl mixture containing 1.6 µM (each) of the primers FIP and BIP, 0.2 µM (each) of the primers F3 and B3, 0.8 µM (each) of the primers LF and LB, 1.2 mM deoxynucleotide triphosphates, 6 mM MgSO4, 1 M betaine, 1× thermopol buffer, 8 U Bst DNA polymerase and 2 µl of DNA template. The reaction was incubated for 45 min at 65° C. and then was terminated by heating at 80° C. for 2 min. Negative and positive controls were included for each LAMP assay.

Visualization Test

After the amplification, 1 µl SYBR Green I was added to each LAMP reaction tube to observe the color change. Since fluorescent dye SYBR Green I binds to double-stranded DNA and produces a yellow fluorescence which can be observed by the naked eye under natural light or under UV lamp. The observation of the yellow/fluorescence color change indicates a positive reaction.

Example 5

Results

Figure 2:
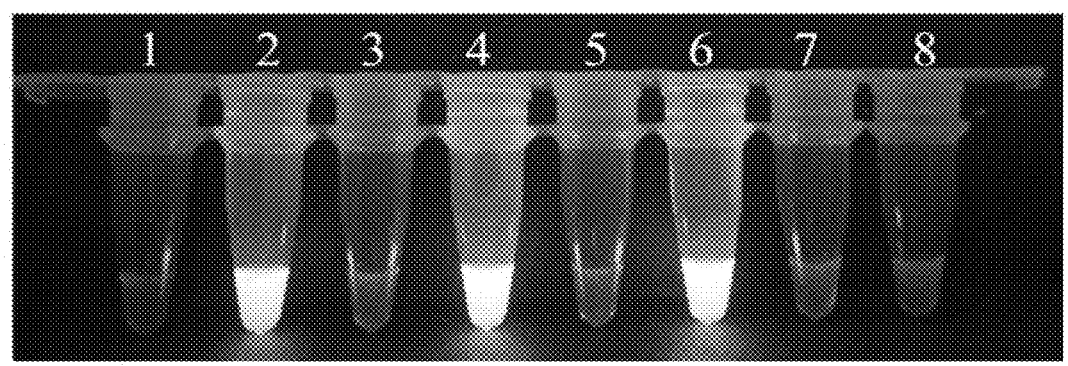
FIG. 2 is a visualization of LAMP amplification products with SYBR Green I (observed by UV light). Fluorescence indicates a positive result and non-fluorescence indicates a negative result.

The developed LAMP assays (as described above) were applied to detect mastitis pathogens in milk using simple low-cost equipment and observed directly by naked eye and under UV light. Application of the LAMP assays was performed on bacterial strains isolated from milk submitted to the Wisconsin Diagnostic Veterinary Laboratory for mastitis testing. DNA was also extracted directly from the milk samples using a commercial kit and applied to the LAMP assays. The results obtained indicate that the LAMP assays are suitable and effective for the detection of E. coli, S. aureus, K. pneumonia, S. uberis, S. dysgalactiae, S. agalactiae, M. bovis, and coagulase-negative Staphylococci (S. epidermidis, S. chromogenes, and S. simulans), the primary pathogens known to cause bovine mastitis. These pathogens could be detected both in pure cultures and directly from milk. FIGS. 1 and 2 illustrate the results of this experiment.

Example 6

Further Results—LAMP Assay Results from Milk and Colonies

We used cow milk submitted to the Wisconsin Veterinary Diagnostic Laboratory for routine bacteriological culture and confirmed our results presented in Examples 1 to 5 using the LAMP assays on DNA extracted from the raw milk and from colonies of bacteria on culture plates. Conclusion: Good agreement as shown in Table 4.

TABLE 4

LAMP Assay Results from Milk and Colonies for five assays of each of the 10 pathogens (recall that 'CNS' represents 3 Coagulase negative *Staphylococcus aureus*) in Example 1 to 5.

| Animal ID | LAMP Result Directly from Milk | LAMP Result from Colonies | WVDL Culture Result | Assays Performed Concurrently |
|---|---|---|---|---|
| Galaxy LR | CNS | CNS | CNS | CNS, Ecoli, Sdys |
| 2233-6 | CNS | CNS | CNS | CNS, Ecoli, Sdys |
| 2297 | CNS | CNS | CNS | CNS, SA, Sdys |
| 2575-4 | CNS | CNS | CNS | CNS, Mbovis, Ecoli |
| 2839 | CNS | CNS | CNS | CNSSA, Sdys |
| 2769 | *E. coli* | *E. coli* | *E. coli* | Ecoli, SA, CNS, S.dys, Sub |
| 3746 | *E. coli* | *E. coli* | *E. coli* | Ecoli, SA, CNS, S.dys, Sub |
| 3308 | *E. coli* | *E. coli* | *E. coli* | Ecoli, SA, CNS, S.dys, Kleb |
| 11727 | *E. coli* | *E. coli* | *E. coli* | Ecoli, SA, CNS, S.dys, Kleb |
| 12213 | *E. coli* | *E. coli* | *E. coli* | Ecoli, SA, CNS, S.dys, Kleb |
| 4103LR | *Kleb. pneumonia* | *Kleb. pneumonia* | *Kleb.*sp. | Kleb, SA, CNS, Ecoli |
| 14659RF | *Kleb. pneumonia* | *Kleb. pneumonia* | *Kleb.* sp. | Kleb, SA, CNS, Ecoli |
| 8627-2 | *Kleb. pneumonia* | *Kleb. pneumonia* | *Kleb.* sp. | Kleb, SA, Sdys |
| 1227LR | *Kleb. pneumonia* | *Kleb. pneumonia* | *Kleb.* sp. | Kleb, SA, Sdys |
| 1159RF | *Kleb. pneumonia* | *Kleb. pneumonia* | *Kleb.* sp. | Kleb, Ecoli, Sdys, Sub |
| 8003 | *M. bovis* | No growth | *M. bovis* | Mbovis, SA |
| 1176 | *M. bovis* | *M. bovis* | *M. bovis* | Mbovis, SA, Ecoli |
| 16169 | *M. bovis* | *M. bovis* | *M. bovis* | Mbovis, SA, Ecoli |
| 47 | *S. agalactiae* | *S. agalactiae* | *S. agalactiae* | Sag, CNS, Sdys, Sub |
| 52 | *S. agalactiae* | *S. agalactiae* | *S. agalactiae* | Sag, CNS, Sdys, Sub |
| 3323-4 | *S. agalactiae* | *S. agalactiae* | *S. agalactiae* | Sag, CNS, Sdys, Sub |
| 9498RR | *S. dysgalactiae* | *S. dysgalactiae* | *S. dysgalactiae* | Sdys, CNS, Sub |
| 11721 | *S. dysgalactiae* | *S. dysgalactiae* | *S. dysgalactiae* | Sdys, SA, CNS, Ecoli, Kleb |
| 30228-1 | *S. dysgalactiae* | *S. dysgalactiae* | *S. dysgalactiae* | Sdys, SA, Sub |
| 30228-2 | *S. dysgalactiae* | *S. dysgalactiae* | *S. dysgalactiae* | Sdys, SA, Sub |
| 30257-1 | *S. dysgalactiae* | *S. dysgalactiae* | *S. dysgalactiae* | Sdys, SA, CNS |
| 4313LF | *S. uberis* | *S. uberis* | *S. uberis* | Sub, Ecoli, Kleb |
| 14987LF | *S. uberis* | *S. uberis* | *S. uberis* | Sub, SA, Sdys, Sub |
| 2007-1 | *S. uberis* | *S. uberis* | *S. uberis* | Sub, SA, Sdys, Sub |
| 14737-3 | *S. uberis* | *S. uberis* | *S. uberis* | Sub, SA, Sdys, Sub |
| 14987LF | *S. uberis* | *S. uberis* | *S. uberis* | Sub, SA, Sdys, Sub |
| 1096 | *Staph. aureus* | *Staph. aureus* | *Staph. aureus* | SA, CNS, Ecoli, Kleb |
| 266 | *Staph. aureus* | *Staph. aureus* | *Staph. aureus* | SA, CNS, Ecoli, Kleb |
| 1512 | *Staph. aureus* | *Staph. aureus* | *Staph. aureus* | SA, CNS, Ecoli, Kleb |
| 1342 | *Staph. aureus* | *Staph. aureus* | *Staph. aureus* | SA, CNS, Ecoli, Kleb |
| 3439RR | *Staph. aureus* | *Staph. aureus* | *Staph. aureus* | SA, CNS, Ecoli, Kleb |
| 5998LR | *Staph. aureus* | *Staph. aureus* | *Staph. aureus* | SA, CNS, Ecoli, Kleb |
| 6569LR | *Staph. aureus* | *Staph. aureus* | *Staph. aureus* | SA, CNS, Ecoli, Kleb |

We next examined preserved milk samples for routine raw milk analysis and confirmation of mastitis pathogens by a commercially available PCR results reference test. Conclusion: the LAMP assays of the present invention matched the PCR results in 8/12 cases, showing good agreement in preserved milk samples as can be found in Table 5.

Milk culture results confirmed the LAMP assay results in 11/12 cases, with the exception of sample AC that should have been LAMP positive for *E. coli* as well. Assays (LAMP and cultures) were performed by Mrs. Marianne Middelveen, Calgary, Canada who runs a routine milk diagnostic lab (see Table 6). Conclusion: good agreement.

TABLE 5

Preserved Milk Sample from AgSource

| Animal ID | *E. coli* | *Kleb. pneumonia* | *M. bovis* | *Staph. aureus* | CNS | SAG | *S. dys* | *S. uberis* | AgSource Pathoproof Result | Agreement |
|---|---|---|---|---|---|---|---|---|---|---|
| Honey | Neg | Neg | Neg | Pos | Neg | Neg | Neg | Neg | *Staph. aureus* High Pos | Yes |
| 910 | Neg | Neg | Neg | Neg | Neg | Neg | Neg | Pos | *S. uberis* Med. Pos | Yes |
| 7341 | Neg | Neg | Pos | Neg | Neg | Neg | Neg | Neg | *M. bovis* High Pos | Yes |
| 2243 | Neg | Neg | Pos | Neg | Neg | Neg | Neg | Neg | *M. bovis* Med. Pos | Yes |
| 87 | Pos | Neg | NT | Neg | Neg | NT | Neg | NT | *E. coli* Suspect | Yes |
| 167 | Pos | Neg | NT | Neg | Neg | NT | Neg | NT | *E. coli* Suspect | Yes |
| 199 | NT | Neg | NT | NT | Neg | NT | Pos | NT | *S. dys* Med. Pos | Yes |
| 1 | Neg | Neg | NT | Neg | Neg | NT | Pos | NT | *S. dys* Med. Pos | Yes |
| 197 | Neg | Neg | NT | Neg | Neg | NT | Neg | NT | *S. dys* Med. Pos | No |
| Pool 6 | Neg | Neg | Neg | Neg | Neg | Neg | Neg | Neg | *S. dys* Med. Pos | No |
| 411 | Neg | Neg | Neg | Neg | Neg | Neg | Neg | Neg | *S. uberis* Med. Pos | No |
| 3715 | Neg | Neg | Neg | Neg | Neg | Neg | Neg | Neg | *M. bovis* Med. Pos | No |

TABLE 6

LAMP Assays Performed by a Canadian Milk Diagnostic Lab

| Animal ID | E. coli | Kleb. pneumonia | M. bovis | Staph. aureus | CNS | SAG | S. dys | S. uberis | Alberta Culture Result |
|---|---|---|---|---|---|---|---|---|---|
| 31 | Neg | Pos | Neg | Pos | Neg | Neg | Neg | Neg | Confirmed |
| 38B | Neg | Neg | Neg | Neg | Neg | Neg | Neg | Neg | Confirmed |
| 39 | Pos | Pos | Neg | Neg | Neg | Neg | Neg | Neg | Confirmed |
| 66 | Neg | Pos | Neg | Neg | Neg | Neg | Neg | Neg | Confirmed |
| 68 | Neg | Pos | Neg | Neg | Neg | Neg | Neg | Neg | Confirmed |
| 73 | Neg | Pos | Neg | Neg | Neg | Neg | Neg | Neg | Confirmed |
| 75 | Neg | Pos | Neg | Neg | Neg | Neg | Neg | Neg | Confirmed |
| 100 | Neg | Pos | Neg | Neg | Neg | Neg | Neg | Neg | Confirmed |
| AA | Neg | Pos | Neg | Neg | Neg | Neg | Neg | Neg | Confirmed |
| AB | Pos | Pos | Neg | Pos | Neg | Neg | Neg | Pos | Confirmed |
| AC | Neg | Pos | Neg | Neg | Neg | Neg | Neg | Pos | Discrepency also E.coli + |
| BB | Neg | Pos | Neg | Pos | Neg | Neg | Neg | Neg | Confirmed |

Example 7

β-lactamase *Staphylococcus aureus* blaR1

A LAMP primer set for detecting β-lactamase blaR1 (GenBank M62650.1), a marker for antimicrobial resistance, comprising the following primers was developed and used to test milk samples where β-lactamase genes were suspected to be present or absent (see Table 7):

F3 primer
(SEQ ID NO: 43)
CAGGTATAGTAAACGGGAAGT

B3 primer
(SEQ ID NO: 44)
ATAACATCCCATTCAGCCATAG

FIP primer
(SEQ ID NO: 45)
CTTTCCATCTGATAAATGTGTAGC-AATGGGTGGTTTGTAGGTTAC

BIP primer
(SEQ ID NO: 46)
CCATCTGGGAAAAATGCTGAA-GGCCATTTAAAACACCCATTTC

TABLE 7

Results of the LAMP for β-lactamase from colonies of milk pathogens known to be positive or negative for this marker of antimicrobial resistance.

| Sample ID | β-lactamase | Lamp β-lactamase | Agreement |
|---|---|---|---|
| Staph. aureus FH | Pos | Pos | Yes |
| Staph. aureus 29213 | Pos | Pos | Yes |
| Staph. aureus 25923 | Neg | Neg | Yes |
| Staph. aureus NB305 | Neg | Neg | Yes |
| Staph. epidermis | Pos | Pos | Yes |
| Kleb. pneumonia | Pos | Pos | Yes |
| Strep. dysgalactiae | Neg | Neg | Yes |
| Strep. agalactiae | Neg | Neg | Yes |
| Strep. uberis | Neg | Neg | Yes |
| E. coli K-12 | Neg | Neg | Yes |
| M. bovis | Neg | Neg | Yes |
| Staph. chromogenes 15 | Neg | Neg | Yes |

The β-lactamase LAMP correctly identified all bacteria tested.

We claim:

1. A LAMP method of simultaneously detecting two or more mastitis pathogens in a sample comprising the steps of
   (a) extracting DNA from the sample;
   (b) amplifying a specific region of each mastitis pathogen by reacting the extracted DNA of step (a) with two or more primer sets selected from the group consisting of (i) a primer set comprising SEQ ID NOs:1-6, (ii) a primer set comprising SEQ ID NOs:7-10, (iii) a primer set comprising SEQ ID NOs:11-16, (iv) a primer set comprising SEQ ID NOs:17-22, (v) a primer set comprising SEQ ID NOs:23-28, (vi) a primer set comprising SEQ ID NOs:29-32, (vii) a primer set comprising SEQ ID NOs:33-38, and (viii) a primer set comprising SEQ ID NOs:39-42, wherein the reaction to amplify the specific region of each mastitis pathogen is performed simultaneously on a single device; and (c) detecting or identifying the presence or absence of the amplified products of at least two mastitis pathogens.

2. The method of claim 1, wherein in step (b) the amplification is performed in a reaction solution comprising
(a) betaine in the concentration range of about 0.5-1.5 M;
(b) dNTP in the concentration range of about 1-1.6 mM;
(c) $Mg^{2+}$ in the concentration range of about 5.5-7 mM; and
(d) Bst DNA polymerase in the concentration range of about 8-10 units.

3. The method of claim 1, wherein the sample is derived from cow's milk.

4. The method of claim 1, wherein the DNA is extracted from a bacterial colony derived from cow's milk.

5. A method of detecting or identifying *Mycoplasma bovis* and *Klebsiella pneumonia* in a sample comprising the steps of
(a) extracting DNA from the sample;
(b) amplifying a specific region of the *Mycoplasma bovis* DNA by reacting in a first container a first portion of the extracted DNA of step (a) with a primer set comprising SEQ ID NOs: 33-38 and amplifying a specific region of the *Klebsiella pneumonia* DNA by reacting in a second container a second portion of the extracted DNA of step (a) with a primer set comprising SEQ ID NOs:11-16, wherein the reaction within the first and second containers to amplify a specific region of the *Mycoplasma bovis* DNA and the *Klebsiella pneumonia* DNA is performed simultaneously in a single device; and
(c) detecting or identifying the presence or absence of the amplified products of *Mycoplasma bovis* and *Klebsiella pneumonia*.

6. The method of claim 5, wherein the sample is derived from cow's milk.

7. A method of detecting or identifying at least two of *Streptococcus uberis, Streptococcus dysgalactiae*, and *Staphylococci* in a sample comprising the steps of
(a) extracting DNA from the sample;
(b) amplifying a specific region of at least two of *Streptococcus uberis, Streptococcus dysgalactiae*, and *Staphylococci* by performing at least two reactions selected from the group consisting of (i) amplifying a specific region of the *Streptococcus uberis* DNA by reacting in a first container a first portion of the extracted DNA of step (a) with a primer set comprising SEQ ID NOs:17-22, (ii) amplifying a specific region of the *Streptococcus dysgalactiae* DNA by reacting in a second container a second portion of the extracted DNA of step (a) with a primer set comprising SEQ ID NOs:23-28, and (iii) amplifying a specific region of the *Staphylococci* DNA by reacting in a third container a third portion of the extracted DNA of step (a) with a primer set comprising SEQ ID NOs:39-42, wherein the at least two reactions are performed simultaneously on a single device; and
(c) detecting or identifying the presence or absence of the amplified products of at least two of *Streptococcus uberis, Streptococcus dysgalactiae*, and *Staphylococci*.

8. The method of claim 7, wherein the sample is derived from cow's milk.

9. A LAMP method of simultaneously detecting two mastitis pathogens in a sample comprising the steps of
extracting DNA from the sample;
providing a reaction solution;
amplifying a specific region of a first mastitis pathogen by reacting in a first container comprising the reaction solution a first portion of the extracted DNA with a primer set comprising SEQ ID NOs:33-38;
amplifying a specific region of a second mastitis pathogen by reacting in a second container comprising the reaction solution a second portion of the extracted DNA with a primer set selected from the group consisting of a primer set comprising SEQ ID NOs:1-6, a primer set comprising SEQ ID NOs:7-10, a primer set comprising SEQ ID NOs:11-16, a primer set comprising SEQ ID NOs:17-22, a primer set comprising SEQ ID NOs:23-28, a primer set comprising SEQ ID NOs:29-32, and a primer set comprising SEQ ID NOs:39-42, wherein the reaction within the first and second containers occurs simultaneously on a single device; and
detecting or identifying the presence or absence of the amplified products of the two mastitis pathogens.

10. The method of claim 9, wherein the reaction solution comprises:
(a) betaine in the concentration range of about 0.5-1.5 M;
(b) dNTP in the concentration range of about 1-1.6 mM;
(c) $Mg^{2+}$ in the concentration range of about 5.5-7 mM; and
(d) Bst DNA polymerase in the concentration range of about 8-10 units.

11. The method of claim 10, wherein the concentration of betaine is about 1 M, the concentration of dNTP is about 1.2 mM, the concentration of $Mg^{2+}$ is about 6 mM, and the concentration of Bst DNA polymerase is about 8 units.

12. The method of claim 10, wherein the reaction solution further comprises an addition selected from the group of nuclease-free $H_2O$ and polymerase buffer.

13. The method of claim 9, wherein the sample is derived from cow's milk.

14. The method of claim 9, wherein the DNA is extracted from a bacterial colony derived from cow's milk.

* * * * *